(12) United States Patent
Akiba

(10) Patent No.: US 6,572,539 B2
(45) Date of Patent: Jun. 3, 2003

(54) LINEAR TRANSMISSION MEMBER DRIVING UNIT FOR ENDOSCOPE

(75) Inventor: Haruo Akiba, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/909,824

(22) Filed: Jul. 23, 2001

(65) Prior Publication Data

US 2002/0047341 A1 Apr. 25, 2002

(30) Foreign Application Priority Data

Sep. 4, 2000 (JP) ........................................ 2000-266437

(51) Int. Cl.7 ................................................ A61B 1/00
(52) U.S. Cl. ........................................ 600/167; 600/168
(58) Field of Search .......................... 600/167, 168, 600/173, 104, 106, 121; 606/1, 167, 170, 171, 173, 180

(56) References Cited

U.S. PATENT DOCUMENTS

| 4,832,047 A |   | 5/1989 | Sepetka et al. |
| 5,007,896 A |   | 4/1991 | Shiber |
| 5,360,432 A |   | 11/1994 | Shturman |
| 5,895,350 A | * | 4/1999 | Hori ........................... 600/109 |
| 6,019,721 A | * | 2/2000 | Holmes et al. ............... 433/29 |
| 6,117,071 A | * | 9/2000 | Ito et al. ..................... 600/118 |
| RE37,356 E  | * | 9/2001 | Hori et al. ..................... 348/65 |
| 6,371,909 B1 | * | 4/2002 | Hoeg et al. .................. 600/112 |
| 6,409,658 B1 | * | 6/2002 | Mitsumori ................... 600/130 |
| 6,422,995 B2 | * | 7/2002 | Akiba ........................ 600/167 |

FOREIGN PATENT DOCUMENTS

| DE | 612408      | 4/1935  |
| GB | 1028327     | 5/1966  |
| JP | 11-326783   | 11/1999 |
| JP | 2000-162509 | 6/2000  |
| JP | 2000-206423 | 7/2000  |

* cited by examiner

Primary Examiner—John P. Leubecker
(74) Attorney, Agent, or Firm—Snider & Associates; Ronald R. Snider

(57) ABSTRACT

In the endoscope, in which a protective tube and a linear transmission member are arranged from a tip end portion to an operating unit, for transmitting rotation of a motor to the tip end portion through the linear transmission member to thereby drive a movable lens for making the observation distance variable, the protective tube is divided into a front-side tube and a rear-side tube having a larger inner diameter than the front-side tube, and these are connected together within the operating unit. Also, the linear transmission member is also divided into a front-side transmission member and a rear-side transmission member having a larger outside diameter, and as regards this rear-side transmission member, there is used a multiple coiled spring formed by winding strands of a predetermined number of threads brought into tight contact in a state, in which space for predetermined intervals is left.

3 Claims, 3 Drawing Sheets

21A, 21B: PROTECTIVE TUBE
27A, 27B: LINEAR TRANSMISSION MEMBER 21A, 21B: PROTECTIVE TUBE
27A, 27B: LINEAR TRANSMISSION MEMBER

LINEAR TRANSMISSION MEMBER DRIVING UNIT FOR ENDOSCOPE

BACKGROUND OF THE INVENTION

This application claims the priority of Japanese Patent Application No. 2000-266437 filed on Sep. 4, 2000 which is incorporated herein by reference.

1. Field of the Invention

The present invention relates to a linear transmission member driving unit for an endoscope, and more particularly to a structure of a driving unit for rotating, by means of a motor, a linear transmission member for changing an observation distance.

2. Description of the Prior Art

In recent years, for the endoscope, there has been proposed an endoscope, to which a mechanism for making an observation distance (or depth of field) variable has been applied (disclosed in, for example, Japanese Patent Laid-Open No. 2000-111806 specification or the like). More specifically, a movable lens for making the observation distance variable is installed in an objective optical system arranged at a tip end portion of the endoscope in such a manner that this movable lens can be driven by means of a linear transmission member consisting of a multiple coiled spring or the like. This linear transmission member is arranged together with a protective tube from the tip end portion to an operating unit of the endoscope, and is coupled to a motor provided within this operating unit. In this respect, the protective tube contains the linear transmission member, whereby it is possible to avoid any interference with other members within the endoscope.

According to such a structure, rotation of the motor is transmitted to a driving unit at the tip end portion by means of the linear transmission member to thereby move the movable lens back and forth through this driving unit, whereby it becomes possible to change the observation distance to be set by the objective optical system. This observation distance is operated by a switch provided in the operating unit or the like so that a focal length can be changed to a far direction or a near direction.

BRIEF SUMMARY OF THE INVENTION

Object of the Invention

In the linear transmission member driving unit for the endoscope, however, the linear transmission member consisting of a multiple coiled spring or the like is contained within the protective tube as described above, and an insertion portion (tip end portion, angle portion and soft portion) of the endoscope is requested to have as fine a diameter as possible, and the protective tube to be arranged within the insertion portion is also formed to be as fine as possible, and therefore, there is a problem that friction between the protective tube and the linear transmission member deteriorates the transmission efficiency of motor rotation.

Also, as the endoscope, various types such as gastroscopes and large intestine scopes have been manufactured, and since each of these endoscopes differs in diameter and length of their insertion portions, the respective protective tubes for them must be also adjusted in diameter and length for each type. On the other hand, on the operating unit side, in which the motor driving unit is arranged, it has been requested to standardize the structure of the driving unit including the protective tube irrespective of the type of the endoscope.

The present invention has been achieved in the light of the above-described problems, and is aimed to provide a linear transmission member driving unit for an endoscope capable of enhancing transmission efficiency of the motor driving force by reducing friction between the linear transmission member and the protective tube as far as possible and making the structure of the driving unit within the operating unit identical even when the endoscope is different in type.

SUMMARY OF THE INVENTION

In order to attain the above-described object, there is provided a linear transmission member driving unit for an endoscope according to the present invention, in which the linear transmission member and a protective tube therefor are arranged from a tip end portion to an operating unit, for rotating the linear transmission member by means of a motor to thereby drive an object at the tip end portion, wherein the protective tube is divided into a front-side tube and a rear-side tube having a larger inner diameter than the front-side tube, and the front-side tube and the rear-side tube are connected together within the operating unit.

Also, the linear transmission member can be also divided into a front-side transmission member and a rear-side transmission member having a larger outside diameter than the front-side transmission member.

Another invention is characterized in that a multiple coiled spring formed by winding strands of a predetermined number of threads brought into tight contact in a state, in which space for predetermined intervals is left, is used as the above-described rear-side transmission member.

According to the above-described structure, in the rear-side tube having a larger inner diameter arranged within the operating unit, friction with the linear transmission member is reduced so that the transmission efficiency of the motor can be enhanced. Also, this rear-side tube has an advantage that it can be made to have a constant thickness irrespective of the type of the endoscope.

According to another invention described above, the rear-side transmission member is to be formed by winding strands every four or five pieces while space for, for example, a single thread is left, and this spiral space for a single thread is capable of reducing the friction between the rear-side transmission member and the protective tube.

DETAILED DESCRIPTION OF THE PREFERRED EMBODIMENTS

Figure 1:
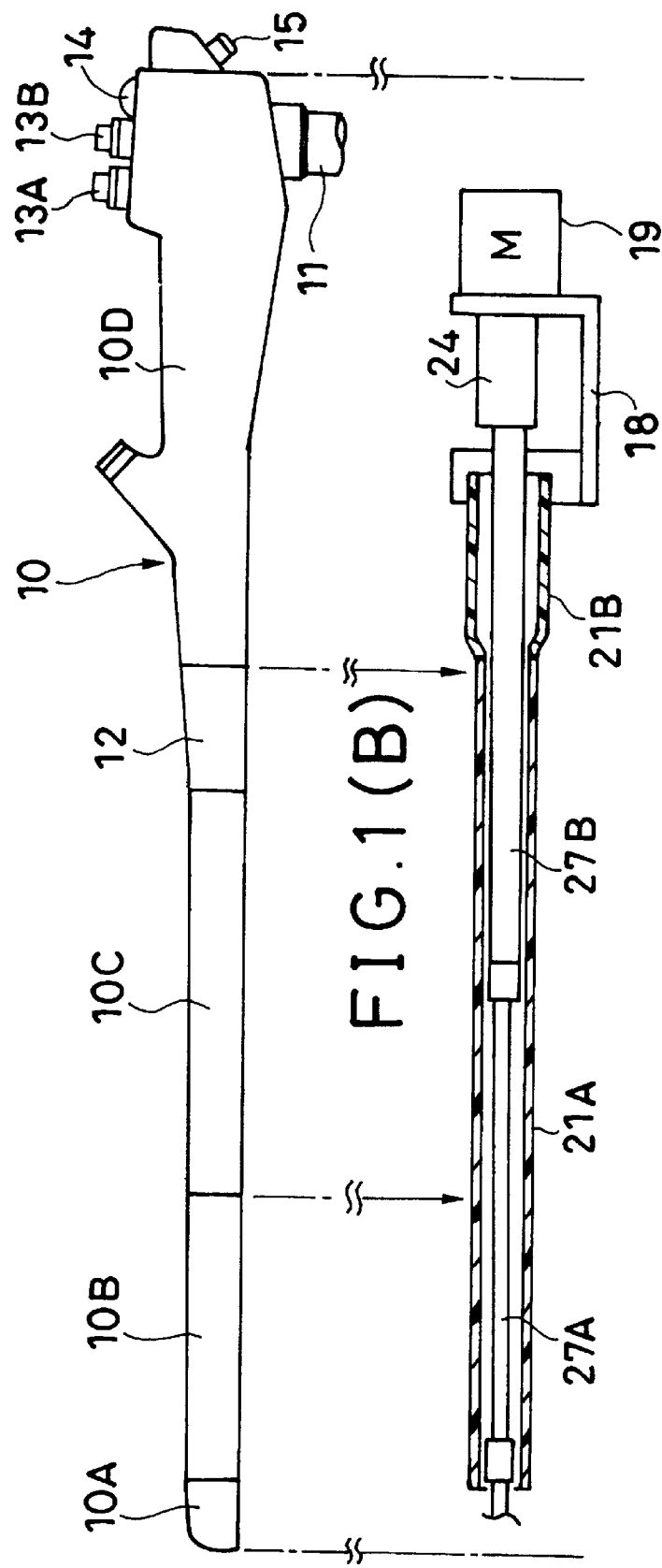
FIG. 1A is a view showing an overall structure of an endoscope according to an embodiment of the present invention. In this respect, an angle portion 10B and a soft portion 10C are drawn with their length reduced.
FIG. 1B is a view showing a structure of a linear transmission member driving unit according to the embodiment.

Each drawing shows a linear transmission member driving unit for an endoscope (electronic endoscope) according to the embodiment, and as shown in FIG. 1A, an endoscope 10 has a tip end portion 10A, an angle portion 10B, a soft portion 10C and an operating unit 10D, and is connected to a processor or the like through a cable 11. At a connecting portion between the operating unit 10D and the soft portion 10C, there is provided cover rubber 12, and in this operating unit 10D, there are arranged an air supply/water supply switch 13A, a suction switch 13B, a photograph switch 14, a switch 15 for making the observation distance variable, or the like.

Figure 4:
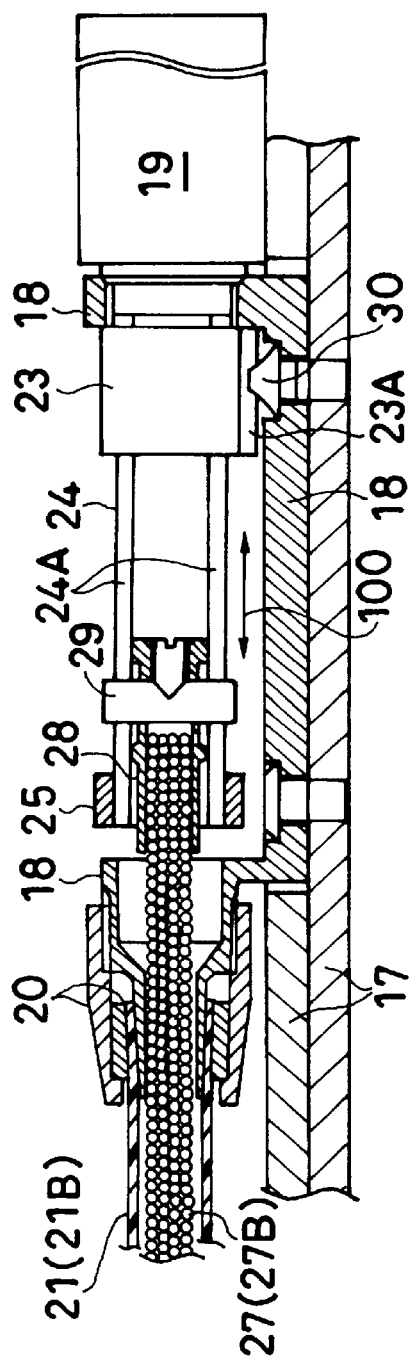
FIG. 4 is a view for a motor driving unit within the operating unit, showing the detail of the driving unit according to the embodiment.
Figure 5:
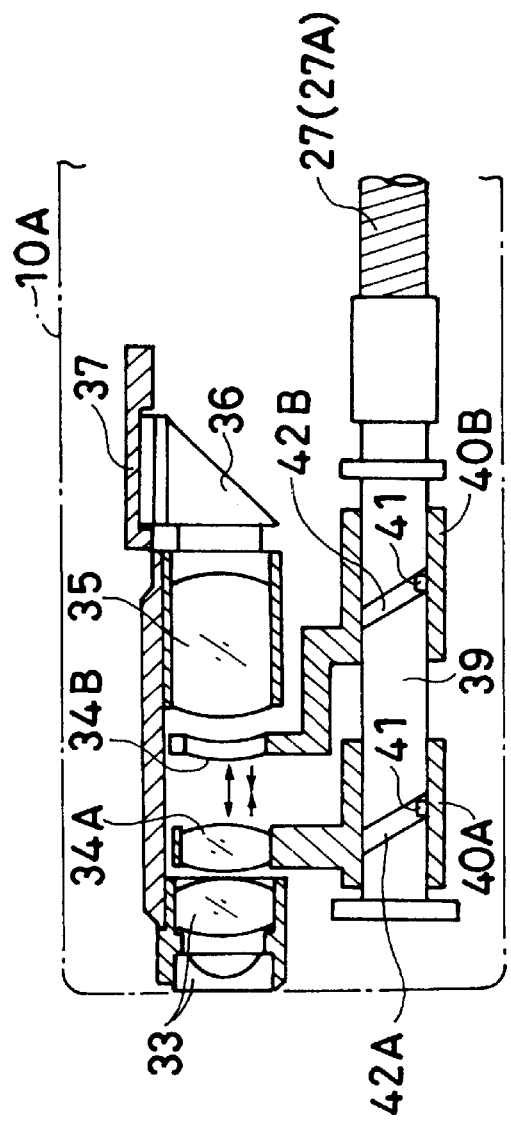
FIG. 5 is a view showing a lens driving unit within a tip end portion of the endoscope according to the embodiment.

FIGS. 4 and 5 show the detail of the interior, and FIG. 4 shows a structure of the motor driving unit within the operating unit 10D. As shown, to a chassis 17, a motor (tip-end side) 19 is mounted through a holding member (rear-side mounting portion) 18 of the driving unit, and to the front-side mounting portion of the holding member 18, there is held and fixed a protective tube 21 containing a net through a fixture 20.

To a rotating shaft of the motor 19, there is mounted a shaft connecting member 24 constituting a movable shaft coupling mechanism by means of a shaft fixing portion 23. More specifically, this shaft connecting member 24 has a main body as a cylindrical element. For example, at two places opposite to each other on a wall of this cylindrical element, there are formed sliding guide holes 24A along the rotating shaft direction 100, and on the tip end side, there is mounted a stopper ring 25. Also, the end portion of a linear transmission member 27 consisting of a multiple coiled spring or the like inserted into the protective tube 21 is fixed to a sleeve 28, which is mounted with a pin 29 in a direction perpendicular to the rotating shaft direction 100.

Therefore, this shaft connecting member 24 transmits the rotation of the motor 19 to the linear transmission member 27, and slides the pin 29 along the guide hole 24A to thereby play a role of moving the rear end of the linear transmission member 27 in the rotating shaft direction 100. As a result, the linear transmission member 27 advances or retracts in response to an angle bending operation not to expand or contract by itself any longer, making it possible to perform a stable driving operation. Also, at the shaft fixing portion 23, there is provided a wall-shaped protruded portion 23A along the axial direction, a locking pin portion 30 for locking this protruded portion 23A is formed as a setscrew. These function as a rotary stopper mechanism, and after securing a predetermined range of rotation of the linear transmission member 27, the rotation of the shaft connecting member 24 is stopped. This stoppage eliminates any kink of the linear transmission member 27 to thereby improve the response of the driving control.

FIG. 5 shows a structure of the lens driving unit within the tip end portion 10A. In this tip end portion 10A, there is provided an objective optical system consisting of a front-side lens 33, two movable lenses 34A and 34B for changing the observation distance, and a rear-side lens 35, and to this objective optical system, there is optically connected a CCD37 through a prism 36. On a holding member for the movable lenses 34A and 34B, there are integrally provided cylindrical portions 40A and 40B having through-holes, through which a rotary driving element 39 coupled to the linear transmission member 27 is inserted.

And, on the inner walls of the cylindrical portions 40A and 40B, there are provided pins 41, and on the outer periphery of the other rotary driving element 39, there are formed cam grooves 42A and 42B for engaging with the pins 41, and this rotary driving element 39 and the cylindrical portions 40A and 40B function as the guide member.

Therefore, when the rotation of the linear transmission member 27 is transmitted to the rotary driving element 39, this rotation is converted into a straight-line motion by means of the engagement between the cam grooves 42A and 42B and the pins 41 of the cylindrical portions 40A and 40B so that the movable lenses 34A and 34B move so as to approach to each other or retract in the optical axial direction. As a result, a scaling operation is performed by the objective optical system.

FIG. 1B shows a layout structure of the protective tube 21 and the linear transmission member 27 which correspond to the endoscope, and in the example concerned, these are divided into two respectively. More specifically, the protective tube 21 is divided into a front-side tube 21A and a rear-side tube 21B having larger diameters (inner diameter and outside diameter) than the front-side tube 21A, and these are connected together within the operating unit 10D. Also, the linear transmission member 27 is also divided into a front-side transmission member 27A and a rear-side transmission member 27B having a larger outside diameter than this front-side transmission member 27A, and these are connected together within the soft portion 10C.

Figure 2:
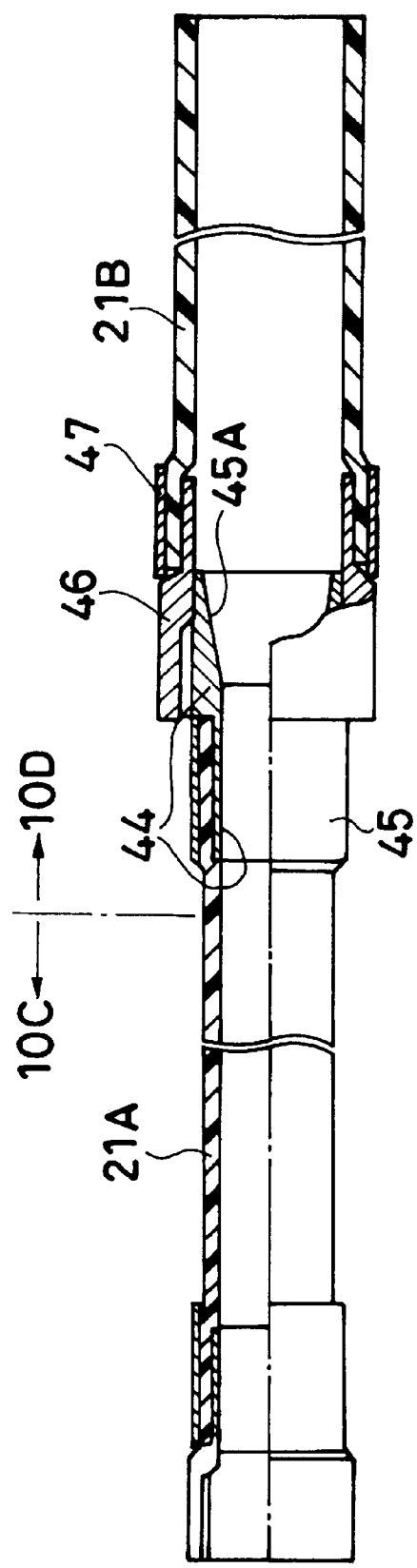
FIG. 2 is a view for a protective tube showing detail of the linear transmission member driving unit for the endoscope of FIG. 1A.

FIG. 2 shows a detail drawing for the protective tube 21A and 21B, and a rear end portion of the front-side tube 21A is fitted in the outer periphery of a first connecting barrel 44 to be bonded with adhesive or the like, and on the outside thereof, a thin-walled pipe 45 as a fastening member is arranged. On the outer periphery of this first connecting barrel 44, there is formed a male threaded portion, and to a second connecting barrel 46, formed with a female threaded portion for threadedly engaging this male threaded portion, having a larger inner diameter than the first connecting barrel 44, there is mounted a rear-side tube 21B. More specifically, in the outer periphery of the second connecting barrel 46, the front end portion of the rear-side tube 21B is fitted, is bonded with adhesive or the like, and the outside thereof is pressed with a thin-walled pipe 47.

Also, on the inner periphery of the rear side of the first connecting barrel 44, there is formed a tapered (conical) surface 45A, which spreads toward the rear end port, in such a manner that there is caused no difference in level within the protective tube 21 by means of the tapered surface 45A. The connecting portion between the tube 21A and the tube 21B based on the first connecting barrel 44 and the second connecting barrel 46 is arranged within the operating unit 10D as described above, and the rear end portion of the rear-side tube 21B is mounted to the holding member 18 of the FIG. 4.

Figure 3:
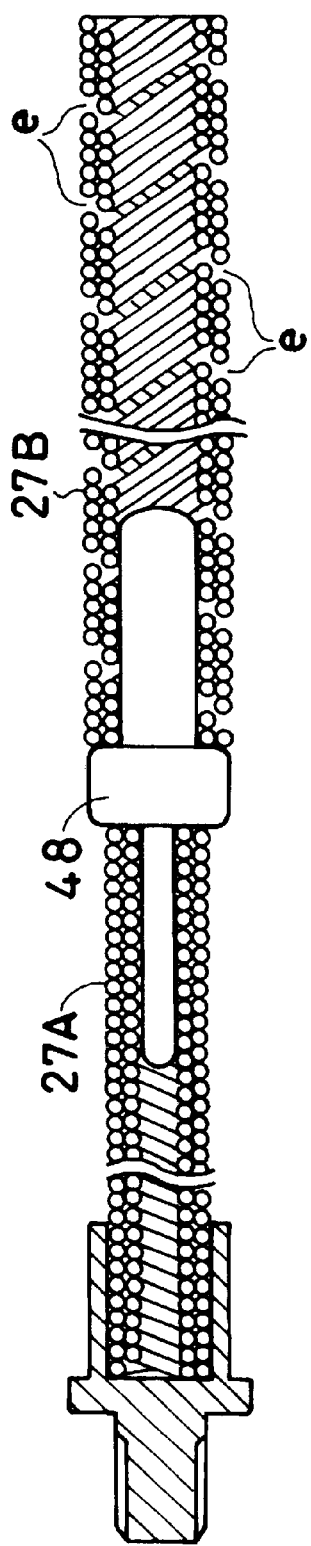
FIG. 3 is a view showing a linear transmission member for the linear transmission member driving unit of FIG. 1B.

FIG. 3 shows a detail drawing for the linear transmission members 27A and 27B, and the front-side transmission member 27A and the rear-side transmission member 27B are connected together through a connecting member 48 as shown. A connecting portion of the linear transmission member 27 using this connecting member 48 is arranged midway in the soft portion 10C as described above. According to the connecting portion, the rotation of the motor 19 can be satisfactorily transmitted to the rotary driving element 39 at the tip end portion 10A by means of stable rotation of the linear transmission member 27.

Also, in the example concerned, the rear-side transmission member 27B is constructed so as to leave space for a single thread. That is, the linear transmission member 27 comprises coiled spring strands wound in multiple ways, and for example, five pieces of strands are wound in a spiral fashion so as to leave space for a single thread (at any intervals) as indicated by "e" in FIG. 3 in a state in which they are brought into tight contact, and this is doubled for formation. In this case, the friction between the rear-side transmission member 27B, which rotates, and the protective tube 21A, 21B becomes less as compared with when no predetermined intervals are left.

According to the structure of the foregoing embodiment, the diameter of the rear-side tube 21B has been made to be larger than the front-side tube 21A to thereby be able to be separately handled, and therefore, the rear-side tube 21B can be used as a standard tube applicable to all with the front-side tube 21A made to have a size responsive to the type of the endoscope. Thereby, a mounting member for the tube 21B concerned explained in FIG. 4 including the rear-side tube 21B, that is, the holding member 18 and the fixture 20 can be caused to have the same structure for all different types of endoscopes.

Also, it is possible to set the inner diameter of the rear-side tube 21B to such size as to smoothly rotate the linear transmission member 27 irrespective of the diameter of the insertion portion, and to enhance the transmission efficiency of rotation of the linear transmission member 27. And yet, in the example concerned, the rear-side transmission member 27B is constructed so as to leave space for a single thread, and the friction between the rear-side transmission member 27B, and the front-side tube 21A and the rear-side tube 21B can be further reduced to further enhance the transmission efficiency of the linear transmission member 27.

In this respect, in the foregoing embodiment, the front-side transmission member 27A and the rear-side transmission member 27B have been connected together within the soft portion 10C, but it may be possible to connect within either the soft portion 10C or the operating unit 10D in the vicinity of the connecting portion between the front-side tube 21A and the rear-side tube 21B.

As described above, according to the present invention, the protective tube is divided into the front-side tube and the rear-side tube having a larger inner diameter than the front-side tube, and the front-side tube and the rear-side tube are connected together within the operating unit, and therefore, there are advantages that the friction between the linear transmission member and the protective tube is reduced as far as possible to thereby enhance the transmission efficiency of the motor driving force and that even when the endoscope is different in type, the structure of the operating unit-side driving unit can be made to be the same.

Also, according to another invention, as the rear-side linear transmission member, there has been used a multiple coiled spring comprising strands of a predetermined number of threads brought into tight contact wound so as to leave space for predetermined intervals, and therefore, the friction between the linear transmission member and the protective tube can be reduced to further enhance the transmission efficiency of the motor driving force.

What is claimed is:

1. A linear transmission member driving unit for an endoscope, comprising:

a motor provided in an operating unit in order to drive an object at a tip end portion of said endoscope;

a linear transmission member for transmitting rotation of said motor to a driving member at said tip end portion; and a protective tube for enveloping said linear transmission member, arranged from said tip end portion to said operating unit, wherein said protective tube is divided into a front-side tube and a rear-side tube having a larger inner diameter than said front-side tube, and said front-side tube and said rear-side tube are connected together within said operating unit, and wherein said linear transmission member is divided into a front-side transmission member and a rear-side transmission member having a larger outside diameter than said front-side transmission member, and said front-side transmission member and said rear-side transmission member are connected between the tip end portion and said operating unit.

2. The linear transmission member driving unit for an endoscope according to the claim 1, wherein a multiple coiled spring formed by winding strands of a predetermined number of threads brought into tight contact in a state, in which space for predetermined intervals is left, is used as said rear-side transmission member.

3. A linear transmission member driving unit for an endoscope, comprising:

a motor provided in an operating unit in order to drive an object at a tip end portion of said endoscope;

a linear transmission member for transmitting rotation of said motor to a driving member at said tip end portion; and a protective tube for enveloping said linear transmission member, arranged from said tip end portion to said operating unit, wherein said protective tube is divided into a front-side tube and a rear-side tube having a larger inner diameter than said front-side tube, and said front-side tube and said rear-side tube are connected together within said operating unit and, wherein a multiple coiled spring formed by winding strands of a predetermined number of threads brought into tight contact in a state, in which space for predetermined intervals is left, is used as a proximal portion of said transmission member.

* * * * *